(12) United States Patent
Miyake et al.

(10) Patent No.: US 10,087,473 B2
(45) Date of Patent: Oct. 2, 2018

(54) METHOD FOR MANUFACTURING CIS-5-HYDROXY-L-PIPECOLIC ACID

(71) Applicant: API CORPORATION, Tokyo (JP)

(72) Inventors: Ryoma Miyake, Kanagawa (JP); Yasumasa Dekishima, Kanagawa (JP)

(73) Assignee: API CORPORATION, Tokyo (JP)

( * ) Notice: Subject to any disclaimer, the term of this patent is extended or adjusted under 35 U.S.C. 154(b) by 0 days.

(21) Appl. No.: 15/526,031

(22) PCT Filed: Nov. 2, 2015

(86) PCT No.: PCT/JP2015/080960
§ 371 (c)(1),
(2) Date: May 11, 2017

(87) PCT Pub. No.: WO2016/076159
PCT Pub. Date: May 19, 2016

(65) Prior Publication Data
US 2017/0306367 A1 Oct. 26, 2017

(30) Foreign Application Priority Data
Nov. 12, 2014 (JP) .................................. 2014-229685

(51) Int. Cl.
*C12N 9/02* (2006.01)
*C12P 17/12* (2006.01)
(52) U.S. Cl.
CPC ............ *C12P 17/12* (2013.01); *C12N 9/0071* (2013.01); *C12Y 114/11* (2013.01)
(58) Field of Classification Search
CPC ........ C12P 17/12; C12Y 114/11; C12N 9/0071
See application file for complete search history.

(56) References Cited

U.S. PATENT DOCUMENTS

| | | | |
|---|---|---|---|
| 9,611,490 B2 * | 4/2017 | Fujii | ........................ C12P 17/12 |
| 2011/0091942 A1 | 4/2011 | Kino et al. | |
| 2013/0330786 A1 | 12/2013 | Kino et al. | |
| 2015/0118719 A1 | 4/2015 | Chen et al. | |
| 2015/0211035 A1 | 7/2015 | Fujii et al. | |

FOREIGN PATENT DOCUMENTS

| WO | 2009/139365 | 11/2009 |
|---|---|---|
| WO | 2013/169725 | 11/2013 |
| WO | 2013/187438 | 12/2013 |

OTHER PUBLICATIONS

Klein et al., Adv. Synth. Catl. 353:1375-1383, 2011.*
Branden et al., Introduction to Protein Structure, Garland Publishing Inc., New York, p. 247.*
Seffernick et al., J. Bacteriol. 183(8):2405-2410, 2001.*
Witkowski et al., Biochemistry 38:11643-11650, 1999.*
Sadowski et al., Current Opinion in Structural Biology 19:357-362, 2009.*
Guo et al., PNAS 101(25):9205-9210, 2004.*
Clifton et al., Eur. J. Biochem. 268:6625-6636, 2001.*
Koketsu et al., "Refined Regio- and Stereoselective Hydroxylation of L-Pipecolic Acid by Protein Engineering of L-Proline cis-4-Hydroxylase Based on the X-ray Crystal Structure", *ACS Synth. Biol.*, 2015, 4(4), pp. 383-392, DOI: 10.1021/sb500247a, published on the web Aug. 29, 2014.
GenBank [online], Accession No. CDG16639, Mar. 7, 2015 uploaded, [retrieved on Jan. 25, 2016], <http://www.ncbi.nlm.nih.gov/protein/CDG16639>, Definition: putative L-proline cis-4-hydroxylase [Xenorhabdus doucetiae].
International Search Report issued in International Patent Application No. PCT/JP2015/080960, dated Feb. 9, 2016.
Notification of Transmittal of Translation of the International Preliminary Report on Patentability (PCT/IB/338 & PCT/IB/373), dated May 26, 2017.
Extended European Search Report issued in EP Patent Application No. 15859618.9, dated Oct. 10, 2017.
Database UniProt [Online], Oct. 1, 2014, Genoscope—CEA, "Putative L-proline cis-4-hydroxylase", Accession No. A0A068QPC1.
Hibi et al., "Novel Enzyme Family Found in Filamentous Fungi Catalyzing trans-4-Hydroxylation of L-Pipecolic Acid", *Applied and Environmental Microbiology*, vol. 82, No. 7, pp. 2070-2077, 2016.
Mattay et al., "Pipecolic Acid Hydroxylases: A Monophyletic Clade among cis-Selective Bacterial Proline Hydroxylases that Discriminates L-Proline" *ChemBioChem*, vol. 18, No. 15, pp. 1523-1528, 2017.

* cited by examiner

*Primary Examiner* — Delia M Ramirez
(74) *Attorney, Agent, or Firm* — Greenblum & Bernstein, P.L.C.

(57) ABSTRACT

A method for producing cis-5-hydroxy-L-pipecolic acid, the method comprising allowing a 2-oxoglutarate-dependent L-pipecolic acid hydroxylase to act on L-pipecolic acid to generate cis-5-hydroxy-L-pipecolic acid, wherein the 2-oxoglutarate-dependent L-pipecolic acid hydroxylase comprises the polypeptide (A), (B) or (C) below: (A) a polypeptide comprising the amino acid sequence represented by SEQ ID NO: 4 or 11; (B) a polypeptide comprising the amino acid sequence represented by SEQ ID NO: 4 or 11 except that one or several amino acids are deleted, substituted, and/or added, which polypeptide has 2-oxoglutarate-dependent L-pipecolic acid hydroxylase activity; or (C) a polypeptide comprising an amino acid sequence with an identity of not less than 60% to the amino acid sequence represented by SEQ ID NO: 4 or 11, which polypeptide has 2-oxoglutarate-dependent L-pipecolic acid hydroxylase activity.

5 Claims, 3 Drawing Sheets
Specification includes a Sequence Listing.

SEQUENCE LISTING

<160> NUMBER OF SEQ ID NOS: 13

<210> SEQ ID NO 1
<211> LENGTH: 882
<212> TYPE: DNA
<213> ORGANISM: Artifical Sequence
<220> FEATURE:
<223> OTHER INFORMATION: xdph_Ecodon

<400> SEQUENCE: 1

```
atgatgagcg caaaactgct ggcaagcatt gaattgaacc aagaacagat cgagcatgat      60
ctgaatattg ttggtagcga gatcctggac gtggcgtaca gcgagtatgc gtgcggcaat     120
tggggtacca ttaccctgtg gaaccacagc ggcgatgctg cgaccagac gagccgcgaa      180 tacgttggtc aggcccgtcc gactgagctg ggccagcaat tagactgcat taatcagctg     240
atccgtaaca atttcaacat cagcctgatc aagagcgtgc gcatcttccg tagctataac     300
ggtggtgcga tctatccgca cattgactac ttggaattca accaaggttt taagcgcgtg     360
cacctggttc tgaaatccga ccgttcatgt ctgaatagcg aagagaacac ggtttatcac     420
atgctgcctg gtgaagtgtg gtttgtcgat ggtcatagcg cgcactcggc gatgagcctg     480
agccgtgtcg gcaagtactc gctggtcctg gactttgatt ctggcgccaa attcgaagat     540
ctgtattctg agagccacac cctgtgtgtt gataacctgg agccggacat tatccatgac     600
cgccagccac tgccgaccag cctgcgtgat agcctggcac acattgctga gcatgcggat     660
gaattcaata tccaatccat tctgttcctg gccacccgtt ttcactttag ctacgcagtg     720
agcattcgtg agtacttcca actcctggac gagtgctttt ctcgcaaccc gtacaagtcc     780
gttcgcgagc gttacgaagc gctgaaagac attttggtgc gtagcggtta taccagccac     840
aatgtcaatc atttcaacag cttgtccggt gtcacgatcg gc                         882
```

<210> SEQ ID NO 2
<211> LENGTH: 843
<212> TYPE: DNA
<213> ORGANISM: Artifical Sequence
<220> FEATURE:
<223> OTHER INFORMATION: smph_Ecodon

<400> SEQUENCE: 2

```
atgagcaccc attttctcgg caaggtaaag tttgatgaag cgcgtttggc agaggacttg    60
agcaccctgg aagtggctga gtttagcagc gcctacagcg actttgcatg cggcaaatgg   120
gaagcgtgcg tcctgcgcaa ccgcaccggt atgcaagaag aagatatcgt tgttagccac   180
aatgctccgg cgctggcgac gccgctgagc aagtccctgc cgtatctgaa cgagctggtg   240
gaaacccatt tcgactgtag cgccgtgcgt tacacgcgca ttgttcgtgt ctctgagaac   300
gcatgtatca ttccgcattc tgactatctg gagttggatg aaacgttcac cgcctgcac    360 ctggttctgg acacgaatag cggttgtgcg aataccgaag aggataagat tttccacatg   420
ggtctgggcg agatctggtt cctggatgct atgctgccgc acagcgccgc atgctttagc   480
aaaactccgc gtctgcactt gatgattgat tcgaggcga ccgcgttccc agagagcttt    540
ttgcgtaacg ttgagcagcc ggtcaccacc cgtgatatgg tggacccgcg taaagagctg   600
accgacgagg tgatcgaagg tatcctgggc ttttccatca tcattagcga ggcaaattac   660
cgtgagattg tctccattct ggcgaaactg cacttctttt acaaggcgga ttgccgcagc   720
atgtacgact ggctgaaaga aatctgcaaa cgtcgtggtg accctgccct gattgaaaag   780
accgcgtcgc tggagcgctt cttcctgggt catcgtgaac gcggtgaggt tatgacgtat   840
taa                                                                 843
```

<210> SEQ ID NO 3
<211> LENGTH: 897
<212> TYPE: DNA
<213> ORGANISM: Artifical Sequence
<220> FEATURE:
<223> OTHER INFORMATION: sruph_Ecodon

<400> SEQUENCE: 3

```
atgaaaagct attccttggg caagtttgag gaccgttcta ttgacagcct gatcgaagaa    60
gcgtccggtc tgccggacag cgcgtattct tctgcgtacc aagagtacag catcggtctg   120
tgggacaccg ccacgctgtg gaacgaacgt ggcaacgaga gcggcgaggt tagcgagcac   180
gcggcagccg ctgcgccgac cgcaattggt cgtagcaccc cgcgtctgaa cgaatttgta   240
cgtgccaagt tcaatgtcga tgtcctgcgt gcggttcgct tgttcagagc gcgtcagggt   300
gcaattatca tcccgcaccg cgattacctg gagcatagca atggttttg ccgtattcac     360 cttccgctgg ttacgacccc gggtgcgcgt aatagcgaga taacgaagt gtatcgcatg   420 ctgcctggcg agctgtggtt cctggattca aacgaagtgc acagcggtgg cgttctggac   480
agcggtacgc gcattcacct cgttttagat ttcacccacg agcataatga gaatccggct   540
gcagtgctga agaacgccga ccgtttgcgt ccgatcgcgc gtgacccgcg catctcgcgc   600
tccaaactgg atcacgaagc gctggagagc ctgatccgcg gtggccgtgt cgtcactctg   660
gcgatgtggc cagctctggt gcagatgctg gcacgcattc atctgaccag cgacgcacat   720
ccggccgagc tgtacgactg gttggatgac ctggcggacc gcagcggcaa cgatgagctg   780
gttgcagaag cgcgtcgtat gcgtcgttac tttctgaccg atggtattag ccgtacgccg   840
agcttcgaac gcttttggcg cgaactggat gccgctcgta aggtgagtt ggtgagc      897
```

<210> SEQ ID NO 4
<211> LENGTH: 294
<212> TYPE: PRT
<213> ORGANISM: Xenorhabdus doucetiae FRM16

<400> SEQUENCE: 4

```
Met Met Ser Ala Lys Leu Leu Ala Ser Ile Glu Leu Asn Gln Glu Gln
1               5                   10                  15

Ile Glu His Asp Leu Asn Ile Val Gly Ser Glu Ile Leu Asp Val Ala
            20                  25                  30

Tyr Ser Glu Tyr Ala Cys Gly Asn Trp Gly Thr Ile Thr Leu Trp Asn
            35                  40                  45

His Ser Gly Asp Ala Gly Asp Gln Thr Ser Arg Glu Tyr Val Gly Gln
50                  55                  60

Ala Arg Pro Thr Glu Leu Gly Gln Gln Leu Asp Cys Ile Asn Gln Leu
65                  70                  75                  80

Ile Arg Asn Asn Phe Asn Ile Ser Leu Ile Lys Ser Val Arg Ile Phe
                85                  90                  95

Arg Ser Tyr Asn Gly Gly Ala Ile Tyr Pro His Ile Asp Tyr Leu Glu
            100                 105                 110

Phe Asn Gln Gly Phe Lys Arg Val His Leu Val Leu Lys Ser Asp Arg
            115                 120                 125

Ser Cys Leu Asn Ser Glu Glu Asn Thr Val Tyr His Met Leu Pro Gly
            130                 135                 140

Glu Val Trp Phe Val Asp Gly His Ser Ala His Ser Ala Met Ser Leu
145                 150                 155                 160

Ser Arg Val Gly Lys Tyr Ser Leu Val Leu Asp Phe Asp Ser Gly Ala
                165                 170                 175

Lys Phe Glu Asp Leu Tyr Ser Glu Ser His Thr Leu Cys Val Asp Asn
            180                 185                 190

Leu Glu Pro Asp Ile Ile His Asp Arg Gln Pro Leu Pro Thr Ser Leu
            195                 200                 205

Arg Asp Ser Leu Ala His Ile Ala Glu His Ala Asp Glu Phe Asn Ile
210                 215                 220

Gln Ser Ile Leu Phe Leu Ala Thr Arg Phe His Phe Ser Tyr Ala Val
225                 230                 235                 240

Ser Ile Arg Glu Tyr Phe Gln Leu Leu Asp Glu Cys Phe Ser Arg Asn
                245                 250                 255

Pro Tyr Lys Ser Val Arg Glu Arg Tyr Glu Ala Leu Lys Asp Ile Leu
            260                 265                 270

Val Arg Ser Gly Tyr Thr Ser His Asn Val Asn His Phe Asn Ser Leu
            275                 280                 285

Ser Gly Val Thr Ile Gly
            290

<210> SEQ ID NO 5
<211> LENGTH: 280
<212> TYPE: PRT
<213> ORGANISM: Sinorhizobium meliloti 1021

<400> SEQUENCE: 5

Met Ser Thr His Phe Leu Gly Lys Val Lys Phe Asp Glu Ala Arg Leu
1               5                   10                  15

Ala Glu Asp Leu Ser Thr Leu Glu Val Ala Glu Phe Ser Ser Ala Tyr
            20                  25                  30

Ser Asp Phe Ala Cys Gly Lys Trp Glu Ala Cys Val Leu Arg Asn Arg
            35                  40                  45

Thr Gly Met Gln Glu Glu Asp Ile Val Val Ser His Asn Ala Pro Ala
50                  55                  60

Leu Ala Thr Pro Leu Ser Lys Ser Leu Pro Tyr Leu Asn Glu Leu Val
65                  70                  75                  80
```

```
Glu Thr His Phe Asp Cys Ser Ala Val Arg Tyr Thr Arg Ile Val Arg
                85                  90                  95

Val Ser Glu Asn Ala Cys Ile Ile Pro His Ser Asp Tyr Leu Glu Leu
            100                 105                 110

Asp Glu Thr Phe Thr Arg Leu His Leu Val Leu Asp Thr Asn Ser Gly
        115                 120                 125

Cys Ala Asn Thr Glu Glu Asp Lys Ile Phe His Met Gly Leu Gly Glu
    130                 135                 140

Ile Trp Phe Leu Asp Ala Met Leu Pro His Ser Ala Ala Cys Phe Ser
145                 150                 155                 160

Lys Thr Pro Arg Leu His Leu Met Ile Asp Phe Glu Ala Thr Ala Phe
                165                 170                 175

Pro Glu Ser Phe Leu Arg Asn Val Glu Gln Pro Val Thr Thr Arg Asp
            180                 185                 190

Met Val Asp Pro Arg Lys Glu Leu Thr Asp Glu Val Ile Glu Gly Ile
        195                 200                 205

Leu Gly Phe Ser Ile Ile Ile Ser Glu Ala Asn Tyr Arg Glu Ile Val
    210                 215                 220

Ser Ile Leu Ala Lys Leu His Phe Phe Tyr Lys Ala Asp Cys Arg Ser
225                 230                 235                 240

Met Tyr Asp Trp Leu Lys Glu Ile Cys Lys Arg Arg Gly Asp Pro Ala
                245                 250                 255

Leu Ile Glu Lys Thr Ala Ser Leu Glu Arg Phe Phe Leu Gly His Arg
            260                 265                 270

Glu Arg Gly Glu Val Met Thr Tyr
        275                 280

<210> SEQ ID NO 6
<211> LENGTH: 299
<212> TYPE: PRT
<213> ORGANISM: Segniliparus rugosus ATCC BAA-974

<400> SEQUENCE: 6

Met Lys Ser Tyr Ser Leu Gly Lys Phe Glu Asp Arg Ser Ile Asp Ser
1               5                   10                  15

Leu Ile Glu Glu Ala Ser Gly Leu Pro Asp Ser Ala Tyr Ser Ser Ala
            20                  25                  30

Tyr Gln Glu Tyr Ser Ile Gly Leu Trp Asp Thr Ala Thr Leu Trp Asn
        35                  40                  45

Glu Arg Gly Asn Glu Ser Gly Glu Val Ser Glu His Ala Ala Ala Ala
    50                  55                  60

Ala Pro Thr Ala Ile Gly Arg Ser Thr Pro Arg Leu Asn Glu Phe Val
65                  70                  75                  80

Arg Ala Lys Phe Asn Val Asp Val Leu Arg Ala Val Arg Leu Phe Arg
                85                  90                  95

Ala Arg Gln Gly Ala Ile Ile Ile Pro His Arg Asp Tyr Leu Glu His
            100                 105                 110

Ser Asn Gly Phe Cys Arg Ile His Leu Pro Leu Val Thr Thr Pro Gly
        115                 120                 125

Ala Arg Asn Ser Glu Asn Glu Val Tyr Arg Met Leu Pro Gly Glu
    130                 135                 140

Leu Trp Phe Leu Asp Ser Asn Glu Val His Ser Gly Gly Val Leu Asp
145                 150                 155                 160

Ser Gly Thr Arg Ile His Leu Val Leu Asp Phe Thr His Glu His Asn
```

```
              165                 170                 175
Glu Asn Pro Ala Ala Val Leu Lys Asn Ala Asp Arg Leu Arg Pro Ile
            180                 185                 190

Ala Arg Asp Pro Arg Ile Ser Arg Ser Lys Leu Asp His Glu Ala Leu
            195                 200                 205

Glu Ser Leu Ile Arg Gly Gly Arg Val Val Thr Leu Ala Met Trp Pro
        210                 215                 220

Ala Leu Val Gln Met Leu Ala Arg Ile His Leu Thr Ser Asp Ala His
225                 230                 235                 240

Pro Ala Glu Leu Tyr Asp Trp Leu Asp Asp Leu Ala Asp Arg Ser Gly
                245                 250                 255

Asn Asp Glu Leu Val Ala Glu Ala Arg Arg Met Arg Arg Tyr Phe Leu
            260                 265                 270

Thr Asp Gly Ile Ser Arg Thr Pro Ser Phe Glu Arg Phe Trp Arg Glu
        275                 280                 285

Leu Asp Ala Ala Arg Lys Gly Glu Leu Val Ser
    290                 295
```

<210> SEQ ID NO 7
<211> LENGTH: 36
<212> TYPE: DNA
<213> ORGANISM: Artifical Sequence
<220> FEATURE:
<223> OTHER INFORMATION: primer

<400> SEQUENCE: 7
tttcatatga gcacccattt tctcggcaag gtaaag        36

<210> SEQ ID NO 8
<211> LENGTH: 33
<212> TYPE: DNA
<213> ORGANISM: Artifical Sequence
<220> FEATURE:
<223> OTHER INFORMATION: primer

<400> SEQUENCE: 8
tttaagcttt taatacgtca taacctcacc gcg        33

<210> SEQ ID NO 9
<211> LENGTH: 858
<212> TYPE: DNA
<213> ORGANISM: Xenorhabdus doucetiae FRM16

<400> SEQUENCE: 9

| | |
|---|---|
| atgagaacgc attttgtggg tgaagttgca ttggacctgg cacgtctgga ggctgatctg | 60 |
| gcaacctgtc gtagcctgga gtggagcgaa gcgtattcgg attacgtctt ggtggtagc | 120 |
| tggaaaagct gcatgctgtg ggcgcctggt ggcgatgccg gcgatggtgt tgtgacggac | 180 |
| tacgcgtacg accgtagcgc gggttttacg ccgcacgcag agcgcctgcc gtatctggca | 240 |
| gagcttattc gtgagactgc agatctggat cgcctgaatt cgcgcgcttt ggcgctggta | 300 |
| accaactctg tgattatccc gcaccgtgac ctgttggaat taagcgactt gccggacgaa | 360 |
| gctcgcaatg aacaccgtat gcacattccg ctggcgacca atgataactg cttcttcaac | 420 |
| gaggacaacg ttgtgtatcg tatgcgtcgt ggtgaagttt ggtttctgga tgccagccgt | 480 |
| attcatagcg tcgctgtcct gacggcgcag ccacgtatcc atctgatgct ggatttcgtg | 540 |
| gacaccccgg gtgcgggcag cttcacgcgc gttgcgggtg gcggcgttga ggccggcatc | 600 |
| ccggtcgatc gcatcgtgac ccgtccgccg ctgggcgacg acgagcgtgc ggacctgttc | 660 |

```
ggtgtcgccc cactcctgtc catggatacc ttcgacgaag tgttttccat tgttatcaag      720
aaacacttcc gtcgtgatgg tggcagcgac tttgtgtggg acaccatgct ggaactggcg      780
gcgaagtctc cggatccggc cgtcctgccg cataccgaag aactgcgcaa gcactacacc      840
ctggaccgca gcgcataa                                                    858
```

<210> SEQ ID NO 10  
<211> LENGTH: 885  
<212> TYPE: DNA  
<213> ORGANISM: Xenorhabdus romanii PR06-A
<400> SEQUENCE: 10

```
atgatgagtg caaaattgtt ggccagcatt gaactgaatc aggaacaaat tgaacacgac       60
ttaaatattg taggtagtga aattctggat gttgcatata gcaatatgc ttgtggcaac      120 tggggcacca tcacgttatg gaatcacagt ggagacgctg gtgaccaaac atcaagagag      180
tatgttgggc aggctcgtcc tacagagctt ggacagcagt tggattgtat taaccaactt      240
attcgaaaca attttaatat atctctgatc aaatcagtgc gtatattccg ttcttataac      300
ggtggagcca tttatccaca tattgattat ttggaattca atcaagggtt caaacgtgtg      360
catctggtgc taaaatcaga ccgaagttgc ctcaattccg aagagaatac agtttatcac      420
atgctccctg gtgaagtatg gtttgttgac ggtcatagtg cacacagtgc aatgtcacta      480
agtcgtgtag ggaaatacag tttagtgctt gattttgact ctggtgctaa attcgaggat      540
ttgtattccg aaagccacac gttatgtgta gacaacctag aaccagatat tattcatgat      600
cggcaaccat tgccaacatc actgcgggat tcactcgctc atatagctga gcacgccgat      660
gaattcaaca ttcagtctat cctgtttctt gctacccgct ttcactttag ttatgcagtg      720
tcaatcagag aatattttca attgttagat gaatgtttta gtcgtaatcc gtacaaatca      780
gttagagaaa gatacgaggc attgaaggat attctagtcc gaagtggcta tacatcccat      840
aagtttaacc actttaactc actgtctgga gtcactattg gttaa                      885
```

<210> SEQ ID NO 11  
<211> LENGTH: 294  
<212> TYPE: PRT  
<213> ORGANISM: Xenorhabdus romanii PR06-A
<400> SEQUENCE: 11

```
Met Met Ser Ala Lys Leu Leu Ala Ser Ile Glu Leu Asn Gln Glu Gln
1               5                   10                  15

Ile Glu His Asp Leu Asn Ile Val Gly Ser Glu Ile Leu Asp Val Ala
            20                  25                  30

Tyr Ser Glu Tyr Ala Cys Gly Asn Trp Gly Thr Ile Thr Leu Trp Asn
        35                  40                  45

His Ser Gly Asp Ala Gly Asp Gln Thr Ser Arg Glu Tyr Val Gly Gln
    50                  55                  60

Ala Arg Pro Thr Glu Leu Gly Gln Gln Leu Asp Cys Ile Asn Gln Leu
65                  70                  75                  80

Ile Arg Asn Asn Phe Asn Ile Ser Leu Ile Lys Ser Val Arg Ile Phe
                85                  90                  95

Arg Ser Tyr Asn Gly Gly Ala Ile Tyr Pro His Ile Asp Tyr Leu Glu
            100                 105                 110

Phe Asn Gln Gly Phe Lys Arg Val His Leu Val Leu Lys Ser Asp Arg
        115                 120                 125
```

```
Ser Cys Leu Asn Ser Glu Glu Asn Thr Val Tyr His Met Leu Pro Gly
    130                 135                 140

Glu Val Trp Phe Val Asp Gly His Ser Ala His Ser Ala Met Ser Leu
145                 150                 155                 160

Ser Arg Val Gly Lys Tyr Ser Leu Val Leu Asp Phe Asp Ser Gly Ala
                165                 170                 175

Lys Phe Glu Asp Leu Tyr Ser Glu Ser His Thr Leu Cys Val Asp Asn
                180                 185                 190

Leu Glu Pro Asp Ile Ile His Asp Arg Gln Pro Leu Pro Thr Ser Leu
            195                 200                 205

Arg Asp Ser Leu Ala His Ile Ala Glu His Ala Asp Glu Phe Asn Ile
        210                 215                 220

Gln Ser Ile Leu Phe Leu Ala Thr Arg Phe His Phe Ser Tyr Ala Val
225                 230                 235                 240

Ser Ile Arg Glu Tyr Phe Gln Leu Leu Asp Glu Cys Phe Ser Arg Asn
                245                 250                 255

Pro Tyr Lys Ser Val Arg Glu Arg Tyr Glu Ala Leu Lys Asp Ile Leu
                260                 265                 270

Val Arg Ser Gly Tyr Thr Ser His Lys Phe Asn His Phe Asn Ser Leu
            275                 280                 285

Ser Gly Val Thr Ile Gly
    290

<210> SEQ ID NO 12
<211> LENGTH: 47
<212> TYPE: DNA
<213> ORGANISM: Artificial Sequence
<220> FEATURE:
<223> OTHER INFORMATION: primer

<400> SEQUENCE: 12
gaattcatta aagaggagaa attaaccatg atgagtgcaa aattgtt                47

<210> SEQ ID NO 13
<211> LENGTH: 47
<212> TYPE: DNA
<213> ORGANISM: Artificial Sequence
<220> FEATURE:
<223> OTHER INFORMATION: primer

<400> SEQUENCE: 13
caacaggagt ccaagctcag ctaattatta accaatagtg actccag                47
```

METHOD FOR MANUFACTURING CIS-5-HYDROXY-L-PIPECOLIC ACID

TECHNICAL FIELD

The present invention relates to a method for producing cis-5-hydroxy-L-pipecolic acid, the method utilizing an enzyme having the ability to produce cis-5-hydroxy-L-pipecolic acid.

BACKGROUND ART

Cis-5-hydroxy-L-pipecolic acid (hereinafter sometimes referred to as "5OH-PA") is a compound useful as an intermediate of pharmaceuticals and the like. It has been known that cis-5-hydroxy-L-pipecolic acid can be produced from L-pipecolic acid by biological approaches.

It has been reported that the BAB52605 protein derived from the root nodule bacterium *Mesorhizobium loti* strain MAFF303099 isolated from *Lotus japonicus* and the CAC47686 protein derived from the root nodule bacterium *Sinorhizobiummeli loti* strain 1021 isolated from *Medicago sativa* (hereinafter sometimes referred to as "SmPH") have the ability to convert L-proline to cis-4-hydroxyproline (Patent Document 1).

It has been reported that the BAB52605 protein has the ability to convert L-pipecolic acid to cis-5-hydroxy-L-pipecolic acid though its production is relatively small (Patent Document 2).

The CAC47686 protein has also been reported to have the ability to convert L-pipecolic acid to cis-5-hydroxy-L-pipecolic acid; however, it produces cis-3-hydroxy-pipecolic acid (hereinafter sometimes referred to as "3OH-PA") as well as cis-5-hydroxy-L-pipecolic acid in an almost equal amount from L-pipecolic acid (Patent Document 2).

Moreover, Patent Document 2 has reported that a *Escherichia coli* (*E. coli*) strain that expresses a protein encoded in a polynucleotide (cis gene), the expression of which is initiated 48 nucleotides (corresponding to 16 amino acids) upstream of the annotation of the EFV12517 protein derived from the *Segniliparus rugosus* strain ATCC BAA-974 (hereinafter sometimes referred to as "SruPH"), has L-pipecolic acid cis-5-hydroxylase activity and is thus able to convert L-pipecolic acid to cis-5-hydroxy-L-pipecolic acid. However, as demonstrated in Examples in this specification, this protein produces cis-3-hydroxy-pipecolic acid in a ratio of around 2%, as well as cis-5-hydroxy-L-pipecolic acid, from L-pipecolic acid.

Patent Document 3 has reported a method for producing cis-5-hydroxy-L-pipecolic acid from L-pipecolic acid. It has been reported in Patent Document 3 that the gene for SmPH is modified to reduce the production of undesirable cis-3-hydroxy-pipecolic acid and the resulting SmPH still produces cis-3-hydroxy-pipecolic acid in a ratio of around 9%.

Non-patent Document 1 has also reported that SmPH produces cis-5-hydroxy-L-pipecolic acid and cis-3-hydroxy-pipecolic acid from L-pipecolic acid. It has been reported in Non-patent Document 1 that the gene for SmPH is modified to increase the production of cis-5-hydroxy-L-pipecolic acid and the resulting SmPH still produces cis-3-hydroxy-pipecolic acid in a ratio of around 4%.

PRIOR ART DOCUMENTS

Patent Documents

Patent Document 1: WO2009/139365
Patent Document 2: WO2013/187438
Patent Document 3: WO2013/169725

Non-Patent Document

Non-patent Document 1: Koketsu et al., ACS Synth. Biol, DOI: 10.1021/sb500247a

SUMMARY OF THE INVENTION

Technical Problem

As described above, methods for producing cis-5-hydroxy-L-pipecolic acid from L-pipecolic acid by biological approaches are known; however, any of those methods is less productive in the production of cis-5-hydroxy-L-pipecolic acid and, moreover, produces cis-3-hydroxy-L-pipecolic acid at some level. Accordingly, there is a demand for a method for producing cis-5-hydroxy-L-pipecolic acid with high purity more efficiently as a method for producing an intermediate of pharmaceuticals and the like, in which high purity is required.

An object of the present invention is to provide a novel method for producing cis-5-hydroxy-L-pipecolic acid with high optical purity more efficiently while producing a less amount of cis-3-hydroxy-L-pipecolic acid.

Solution to Problem

The inventors intensively studied to solve the above-described problems and consequently found that a protein derived from the *Xenorhabdus doucetiae* strain FRM16 (hereinafter sometimes referred to as "XdPH") and a protein derived from the *Xenorhabdus romanii* strain PR06-A (hereinafter sometimes referred to as "XrPH") have high cis-5-hydroxylase activity toward L-pipecolic acid. The inventors also found that cis-5-hydroxy-L-pipecolic acid can be produced with high optical purity and at a high concentration by preparing a transformant using DNA encoding each of these proteins and then allowing the transformed cell, a processed product thereof, and/or a culture liquid thereof to act on L-pipecolic acid. The present invention was achieved based on these findings.

That is, the present invention can be summarized as follows.

[1] A method for producing cis-5-hydroxy-L-pipecolic acid, the method comprising allowing a 2-oxoglutarate-dependent L-pipecolic acid hydroxylase, a microorganism or cell having the ability to produce the enzyme, a processed product of the microorganism or cell, and/or a culture liquid comprising the enzyme and obtained by culturing the microorganism or cell, to act on L-pipecolic acid to generate cis-5-hydroxy-L-pipecolic acid, wherein the 2-oxoglutarate-dependent L-pipecoic acid hydroxylase comprises the polypeptide (A), (B) or (C) below:

(A) a polypeptide comprising the amino acid sequence represented by SEQ ID NO: 4 or 11;

(B) a polypeptide comprising the amino acid sequence represented by SEQ ID NO: 4 or 11 except that one or several amino acids are deleted, substituted, and/or added, which polypeptide has 2-oxoglutarate-dependent L-pipecolic acid hydroxylase activity; or (C) a polypeptide comprising an amino acid sequence with an identity of not less than 60% to the amino acid sequence represented by SEQ ID NO: 4 or 11, which polypeptide has 2-oxoglutarate-dependent L-pipecolic acid hydroxylase activity,

[2] The method for producing cis-5-hydroxy-L-pipecolic acid according to [1], wherein DNA encoding the 2-oxoglutarate-dependent L-pipecolic acid hydroxylase comprises the DNA (D), (E) or (F) below:

(D) DNA comprising the nucleotide sequence represented by SEQ ID NO: 1, 9, or 10;

(E) DNA comprising the nucleotide sequence represented by SEQ ID NO: 1, 9, or 10 except that one or several nucleotides are substituted, deleted, and/or added, which DNA encodes a polypeptide having 2-oxoglutarate-dependent L-pipecolic acid hydroxylase activity; or (F) DNA comprising a nucleotide sequence which hybridizes with the complementary strand of the nucleotide sequence represented by SEQ ID NO: 1, 9, or 10 under stringent conditions, which DNA encodes a polypeptide having 2-oxoglutarate-dependent L-pipecolic acid hydroxylase activity.

[3] The method for producing cis-5-hydroxy-L-pipecolic acid according to [1] or [2], wherein the 2-oxoglutarate-dependent L-pipecolic acid hydroxylase, the microorganism or cell having the ability to produce the enzyme, the processed product of the microorganism or cell, and/or the culture liquid comprising the enzyme and obtained by culturing the microorganism or cell is/are allowed to act on said. L-pipecolic acid in the presence of 2-oxoglutaric acid and ferrous ion.

[4] A 2-oxoglutarate-dependent L-pipecolic acid hydroxylase protein having an activity to act on L-pipecolic acid to generate cis-5-hydroxy-L-pipecolic acid and comprising the polypeptide (A), (B) or (C) below:

(A) a polypeptide comprising the amino acid sequence represented by SEQ ID NO: 4 or 11;

(B) a polypeptide comprising the amino acid sequence represented by SEQ ID NO: 4 or 11 except that one or several amino acids are deleted, substituted, and/or added, which polypeptide has 2-oxoglutarate-dependent L-pipecolic acid hydroxylase activity; or (C) a polypeptide comprising an amino acid sequence with an identity of not less than 60% to the amino acid sequence represented by SEQ NO: 4 or 11, which polypeptide has 2-oxoglutarate-dependent L-pipecolic acid hydroxylase activity.

[5] A polypeptide comprising the amino acid sequence represented by SEQ ID NO: 11.

Advantageous Effect of the Invention

According to the present invention, cis-5-hydroxy-L-pipecolic acid with high optical purity can be produced more efficiently from L-pipecolic acid; furthermore, cis-5-hydroxy-L-pipecolic acid with high purity can be produced at low cost in industrial scale production because a lesser amount of cis-3-hydroxy-L-pipecolic acid is produced.

DESCRIPTION OF THE EMBODIMENTS

Figure 1:
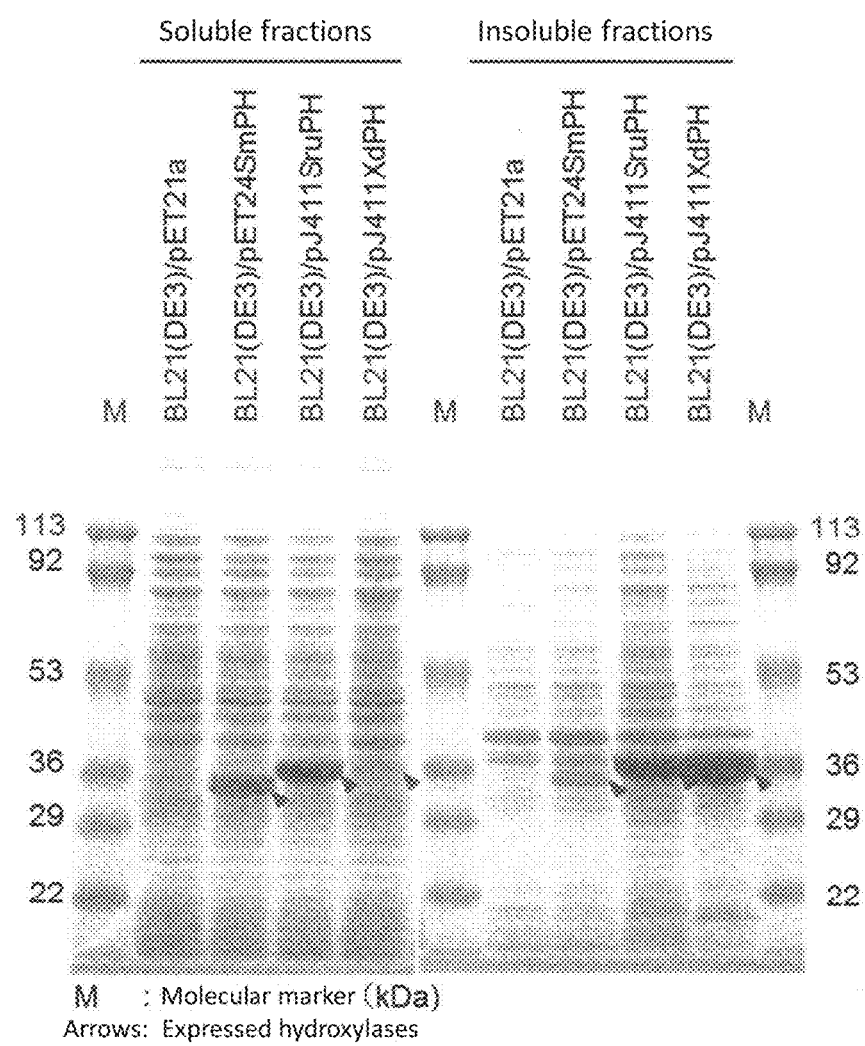
FIG. 1 shows the result of SDS-polyacrylamide electrophoresis (electrophoresis photograph) of extracts from *E. coli* strains to which different L-pipecolic acid hydroxylase genes have been introduced. Arrows indicate the bands corresponding to the L-pipecolic acid hydroxylases.

Now, the present invention will be described below in detail.

In the present specification, "the ability to convert L-pipecolic acid to cis-5-hydroxy-L-pipecolic acid" means the ability to add a hydroxy group to the carbon atom at position 5 of L-pipecolic acid in a 2-oxoglutarate-dependent fashion.

Whether or not "the ability to convert L-pipecolic acid to cis-5-hydroxy-L-pipecolic acid" is retained in a measurement subject can be confirmed by allowing an enzyme, which is a measurement subject, to act on L-pipecolic acid, for example, in a reaction system that contains L-pipecolic acid as a substrate and additionally 2-oxoglutaric acid as a coenzyme, and then directly measuring the amount of cis-5-hydroxy-L-pipecolic acid which has been converted from L-pipecolic acid.

Moreover, the term "enzyme" in the present specification includes a purified enzyme (including a partially purified enzyme), and an enzyme immobilized using a known immobilization technique, including, for example, an enzyme immobilized on a carrier such as polyacrylamide and carrageenan gels, and the like.

In the present specification, a "microorganism or cell having the ability to convert L-pipecolic acid to cis-5-hydroxy-L-pipecolic acid" (hereinafter sometimes referred to as a "microorganism or cell or the present invention") is not particularly limited as long as it has "the ability that enables a hydroxy group to be added to the carbon atom at position 5 of L-pipecolic acid", but the microorganism or cell may be a microorganism or cell that endogenously has the aforementioned ability or a microorganism or cell to which the aforementioned ability has been imparted through any breeding process. Known methods such as recombinant gene technology (transformation) and mutagenesis may be employed as the procedure to impart the aforementioned ability through any breeding process. Several different methods may be used as the method of transformation, in which the expression of a gene of interest is enhanced by the introduction of the gene of interest, by the modification of an expression regulatory sequence thereof on the chromosome, such as a promoter, or the like.

In addition, the type of "the microorganism or cell" includes those in the list of host organisms or host cells described below. Moreover, in the present specification, "the microorganism or cell having the ability that enables a hydroxy group to be added to the carbon atom at position 5 of L-pipecolic acid" is not limited to a living microorganism or cell but includes those apparently dead as living bodies and retaining the ability of the enzyme.

In the present specification, the type of an organism used as "the host organism" is not particularly limited but examples of the organism include prokaryotes such as *E. coli, Bacillus subtilis*, coryneform bacteria, bacteria belonging to the genera *Pseudomonas, Bacillus, Rhizobium, Lactobacillus, Succinobacillus, Anaerobiospirillum, Actinobacillus*, and the like and eukaryotes including fungi, such as yeasts, filamentous fungi and the like, plants, animals, and the like. Among them, *E. coli*, yeasts, and coryneform bacteria are preferable, and *E. coli* is particularly preferable.

In the present specification, the type of a cell used as "the host cell" is not particularly limited but animal cells, plant cells, insect cells and the like can be used.

In the present specification, the term "expression vector" refers to a genetic element that is used for the introduction of a polynucleotide encoding a protein with a desired function to a host organism to be recombined, followed by the replication of the polynucleotide and the expression of the protein with the desired function in the host organism. Examples of the expression vector include, but not limited to, plasmid, virus, phage, cosmid, and the like. Preferably, the expression vector is plasmid.

In the present specification, the term "transformant" means a microorganism or cell to which a gene of interest has been introduced using, for example, an expression vector, such as those as described above, to allow the microorganism or cell to exhibit a desired phenotype associated with its protein with a desired function.

In the present specification, a "processed product of the microorganism or cell" means a product that is prepared by culturing the microorganism or cell and then 1) treating the microorganism or cell with an organic solvent and the like, 2) freeze-drying the microorganism or cell, 3) immobilizing the microorganism or cell on a carrier and the like, or 4) physically or enzymatically disrupting the microorganism or cell, and contains a protein with a desired function.

In the present specification, a "culture liquid comprising the enzyme and obtained by culturing the microorganism or cell" means 1) a culture liquid of the microorganism or cell, 2) a culture liquid obtained by treating the culture liquid of the microorganism or cell with an organic solvent and the like, and 3) a culture liquid in which the cell membrane of the microorganism or cell has been physically or enzymatically disrupted.

The Method for Producing
cis-5-hydroxy-L-pipecolic Acid Using a
2-oxoglutarate-Dependent L-Pipecolic Acid
Hydroxylase The method of the present invention for producing cis-5-hydroxy-L-pipecolic acid is characterized by allowing a 2-oxoglutarate-dependent L-pipecolic acid hydroxylase, a microorganism or cell having the ability to produce the enzyme, a processed product of the microorganism or cell, and/or a culture liquid comprising the enzyme and obtained by culturing the microorganism or cell, to act on L-pipecolic acid. The production method of the present invention is preferably carried out in the presence of 2-oxoglutaric acid and ferrous ion, as described below.

Since the 2-oxoglutarate-dependent L-pipecolic acid hydroxylase used in the present invention (hereinafter sometimes referred to as "the L-pipecolic acid hydroxylase of the present invention") shows high degrees of regiospecificity and stereospecificity in the hydroxylation of L-pipecolic acid, cis-5-hydroxy-L-pipecolic acid with high optical purity can be efficiently obtained by using this enzyme.

The 2-oxoglutarate-dependent L-pipecolic acid hydroxylase of the present invention is not particularly limited as long as it is an enzyme having the ability to convert L-pipecolic acid to cis-5-hydroxy-L-pipecolic acid, but the 2-oxoglutarate-dependent L-pipecolic acid hydroxylase preferably has the amino acid sequence represented by SEQ ID NO: 4 or 11, or is a homologue of the amino acid sequence, which has 2-oxoglutarate-dependent L-pipecolic acid hydroxylase activity. That is, the L-pipecolic acid hydroxylase of the present invention preferably comprises the polypeptide (A), (B) or (C) below:

(A) a polypeptide having the amino acid sequence represented by SEQ ID NO: 4 or 11;

(B) a polypeptide having the amino acid sequence represented by SEQ ID NO: 4 or 11 except that one or several amino acids are deleted, substituted, and/or added, which polypeptide has 2-oxoglutarate-dependent L-pipecolic acid hydroxylation activity; or (C) a polypeptide having an amino acid sequence with an identity of not less than 60% to the amino acid sequence represented by SEQ ID NO: 4 or 11, which polypeptide has 2-oxoglutarate-dependent L-pipecolic acid hydroxylation activity.

Examples of the homologue of the 2-oxoglutarate-dependent L-pipecolic acid hydroxylase having the amino acid sequence represented by SEQ ID NO: 4 or 11, which can be used in the present invention, include, as described above in (B), a polypeptide having the amino acid sequence represented by SEQ ID NO: 4 or 11 except that one or several amino acids are deleted, substituted, and/or added as long as the polypeptide retains 2-oxoglutarate-dependent L-pipecolic acid hydroxylation activity. The term "one or several amino acids" herein means, for example, 1 to 100, preferably 1 to 50, more preferably 1 to 20, still more preferably 1 to 10, and particularly preferably 1 to 5, amino acids.

Moreover, as described above in (C), the above-described homologue may also be a protein with a sequence identity of at least not less than 60%, preferably not less than 80%, more preferably not less than 90%, still more preferably not less than 95%, and particularly preferably not less than 99%, to the entire amino acid sequence of SEQ ID NO: 4 or 11 as long as the protein has 2-oxoglutarate-dependent L-pipecolic acid hydroxylation activity.

The amino acid sequence represented by SEQ ID NO: 4 is based on the known genomic information of the *Xenorhabdus doucetiae* strain FRM16.

The amino acid sequence represented by SEQ ID NO: 11 is based on the information of a gene cloned from the *Xenorhabdus romanii* strain PR06-A by a known method using PCR.

Since the L-pipecolic acid hydroxylase of the present invention, including the amino acid sequence of SEQ ID NO: 4 or 11 and homologues thereof, selectively hydroxylates the carbon atom at position 5 of L-pipecolic acid, it can produce cis-5-hydroxy-L-pipecolic acid with high efficiency.

In addition, multiple different 2-oxoglutarate-dependent L-pipecolic acid hydroxylases may be used in combination in the production method of the present invention.

The 2-oxoglutarate-dependent L-pipecolic acid hydroxylase that can be used in the present invention can be obtained by purifying the enzyme from the *Xenorhabdus doucetiae* strain FRM16 or the *Xenorhabdus romanii* strain PR06-A, while the enzyme can also be obtained by cloning the DNA encoding the 2-oxoglutarate-dependent L-pipecolic acid hydroxylase gene with a known method, such as PCR or hybridization, and then allowing the cloned DNA to be expressed in an appropriate host.

Examples of the DNA that encodes the 2-oxoglutarate-dependent L-pipecolic acid hydroxylase having the amino acid sequence represented by SEQ ID NO: 4 or 11 include DNAs each containing the nucleotide sequence of SEQ ID NO: 1, 9, or 10 and may also include homologues of the DNA containing the nucleotide sequence of SEQ ID NO: 1, 9, or 10 as long as those homologues encode a protein having 2-oxoglutarate-dependent L-pipecolic acid hydroxylation activity. That is, examples of the DNA encoding the L-pipecolic acid hydroxylase of the present invention include the nucleotide sequence (D), (E) or (F) below:

(D) DNA having the nucleotide sequence represented by SEQ ID NO: 1, 9, or 10;

(E) DNA comprising the nucleotide sequence represented by SEQ ID NO: 1, 9, or 10 except that one or several nucleotides are substituted, deleted, and/or added, which DNA encodes a polypeptide having 2-oxoglutarate-dependent L-pipecolic acid hydroxylase activity; or (F) DNA comprising a nucleotide sequence which hybridizes with the complementary strand of the nucleotide sequence represented by SEQ ID NO: 1, 9, or 10 under stringent conditions, which DNA encodes a polypeptide having 2-oxoglutarate-dependent L-pipecolic acid hydroxylase activity.

Examples of the homologue include, as described in (E), variants comprising the nucleotide sequence of SEQ ID NO: 1, 9, or 10 except that one or several nucleotides are substituted, deleted, or added. The term "one or several nucleotides" herein means, for example, 1 to 300, preferably 1 to 150, more preferably 1 to 60, still more preferably 1 to 30, and particularly preferably 1 to 15, nucleotides.

In addition, SEQ ID NO: 1 represents the nucleotide sequence of a gene codon-optimized for expression in *E. coli*, which is a gene encoding the amino acid sequence of SEQ ID NO: 4 from the *Xenorhabdus doucetiae* strain FRM16. Such DNA with codon-optimization according to the host for transformation is, of course, included in examples of DNA encoding the 2-oxoglutarate-dependent L-pipecolic acid hydroxylase that can be used in the present invention.

Furthermore, the homologue of the above-described DNA may also be, as described in (F), DNA which hybridizes with the complementary strand of the nucleotide sequence represented by SEQ ID NO: 1, 9, or 10 under stringent conditions, as long as it encodes a polypeptide having 2-oxoglutarate-dependent L-pipecolic acid hydroxylase activity. The phrase "nucleotide sequence which hybridizes under stringent conditions" herein means the nucleotide sequence of DNA that is obtained by using a DNA probe and using colony hybridization, plaque hybridization, or Southern blot hybridization or the like under stringent conditions. Examples of the stringent conditions can include, in cases of colony hybridization and plaque hybridization, conditions where filters immobilized with DNA from colonies or plaques, or with DNA fragments thereof are used to perform hybridization at 65° C. in the presence of 0.7 mol/L to 1.0 mol/L sodium chloride aqueous solution and the filters are subsequently washed under a temperature condition of 65° C. by using 0.1 to 2×SSC solution (the composition of 1×SSC: 150 mmol/L sodium chloride aqueous solution, 15 mmol/L sodium citrate aqueous solution).

Each of the hybridization methods may be performed in accordance with the methods described in Molecular Cloning: A laboratory Manual, 2nd Ed., Cold Spring Harbor Laboratory, Cold Spring Harbor, N.Y., 1989; and the like.

Those skilled in the art could obtain the DNA homologue as described above by introducing a substitution, deletion, insertion, and/or addition mutation(s) as appropriate to the DNA of SEQ ID NO: 1, 9, or 10 using site-directed mutagenesis (Nucleic Acids Res. 10, pp. 6487 (1982); Methods in Enzymol. 100, pp. 448 (1983); Molecular Cloning, PCR: A Practical Approach, IRL Press, pp. 200 (1991)) or the like.

Moreover, the amino acid information of the 2-oxoglutarate-dependent L-pipecolic acid hydroxylase or the nucleotide sequence information of DNA encoding the same may be obtained by a homology search of the entire or part of the amino acid sequence of SEQ ID NO: 4 or 11, or the entire or part of the nucleotide sequence represented by SEQ ID NO: 1, 9, or 10, against databases such as DNA Databank of JAPAN (DDBJ).

In the method of the present invention for producing hydroxy-L-pipecolic acid, the 2-oxoglutarate-dependent L-pipecolic acid hydroxylase may be directly used for the reaction, but it is preferable to use a microorganism or cell containing the 2-oxoglutarate-dependent L-pipecolic acid hydroxylase, a processed product of the microorganism or cell, and/or a culture liquid comprising the enzyme and obtained by culturing the microorganism or cell.

As the microorganism or cell containing the 2-oxoglutarate-dependent pipecolic acid hydroxylase, a microorganism or cell inherently having the 2-oxoglutarate-dependent L-pipecolic acid hydroxylase may be used but it is preferable to use a microorganism or cell which has been transformed with the gene encoding the 2-oxoglutarate-dependent L-pipecolic acid hydroxylase.

Moreover, as the processed product of the microorganism or cell containing the 2-oxoglutarate-dependent L-pipecolic acid hydroxylase, any of the following can be used: for example, processed products of the microorganism or cell, such as those prepared by treating the microorganism or cell with an organic solvent such as acetone, dimethyl sulfoxide (DMSO), toluene or the like, and/or with a surfactant, those prepared by freeze-drying the microorganism or cell, and those prepared by physically or enzymatically disrupting the microorganism or cell; a crude or purified extract containing an enzyme fraction from the microorganism or cell; and, furthermore, those products immobilized on a carrier represented by polyacrylamide and carrageenan gels; and the like.

As the culture liquid obtained by culturing the microorganism or cell containing the 2-oxoglutarate-dependent L-pipecolic acid hydroxylase, any of the following can be used: for example, a suspension of the microorganism or cell and a liquid medium; and in cases where the microorganism or cell is a microorganism or cell for secretory expression, the supernatant obtained by removing the microorganism or cell by centrifugation and the like, and a concentrate of the supernatant.

A 2-oxoglutarate-dependent L-pipecolic acid hydroxylase-expression vector is provided by insertion of the DNA encoding the 2-oxoglutarate-dependent L-pipecolic acid hydroxylase isolated as described above into a known expression vector in such a way that expression of the DNA is possible. Then, a transformant into which the DNA encoding the 2-oxoglutarate-dependent L-pipecolic acid hydroxylase has been introduced can be obtained by transforming a host cell with this expression vector. The transformant can also be obtained by incorporation of the DNA encoding the 2-oxoglutarate-dependent L-pipecolic acid hydroxylase into the host chromosomal DNA in such a way that expression of the isolated DNA is possible, which incorporation is mediated by a procedure such as homologous recombination or the like.

Specific examples of the method for preparing the transformant include a method in which the DNA encoding the 2-oxoglutarate-dependent L-pipecolic acid hydroxylase is introduced into a plasmid vector, phage vector, or virus vector that stably exists in a host cell, such as a microorganism, and then the constructed expression vector is introduced into the host cell, or a method in which the DNA is directly introduced into the host genome, in either of which methods the genetic information on the DNA is then transcribed and translated. In this process, it is preferable to link a promoter to the DNA on the 5'-upstream side and it is more preferable to further link a terminator to the DNA on the 3'-downstream side, which promoter and terminator are suitable in the host. Such a promoter and terminator are not particularly limited as long as the promoter and terminator are known to be functional in a cell to be used as a host. For example, "Fundamental Microbiology 8: Genetic Engineering, KYORITSU SHUPPAN CO., LTD." describes details of vectors, promoters, and terminators that can be used in host microorganisms.

The host microorganism to be transformed for the expression of 2-oxoglutarate-dependent L-pipecolic acid hydroxylase is not particularly limited as long as the host itself does not adversely affect the reaction of L-pipecolic acid, but specific examples of the host microorganism can include the following microorganisms:

bacteria belonging to the genera *Escherichia, Pseudomonas, Serratia, Brevibacterium, Corynebacterium, Streptococcus, Lactobacillus*, and the like whose host vector systems have been established;

actinomycetes belonging to the genera *Rhodococcus, Streptomyces*, and the like whose host vector systems have been established; yeasts belonging to the genera *Saccharomyces, Kluyveromyces, Schizosaccharomyces, Zygosaccharomyces, Yarrowia, Trichosporon, Rhodosporidium, Hansenula, Pichia, Candida*, and the like whose host vector systems have been established; and molds belonging to the genera *Neurospora, Aspergillus, Cephalosporium, Trichoderma*, and the like whose host vector systems have been established.

The procedure for establishing the transformant, the method for constructing a recombinant vector suitable for the host, and the method for culturing the host can be carried out in accordance with techniques conventionally used in the fields of molecular biology, bioengineering and genetic engineering (for example, methods described in Molecular Cloning).

Specific examples of preferable host microorganisms and of a preferable transformation procedure, vector, promoter, terminator, and the like for each microorganism will be described below. However, the present invention is not limited to thereto.

For the genus *Escherichia*, especially *Escherichia coli*, examples of the plasmid vector include pBR-type and pUC-type plasmids, and examples of the promoter include promoters derived from lac (β-galactosidase), trp (tryptophan operon), tac, trc (fusion of lac and trp), and λ phage PL and PR. Examples of the terminator include terminators derived from trpA, phages, and rrnB ribosomal RNA.

For the genus *Bacillus*, examples of the vector can include pUB110-type plasmids and pC194-type plasmids, which may be integrated into the chromosome. As the promoter and the terminator, those of genes for enzymes, such as alkaline protease, neutral protease, and α-amylase, can be used.

For the genus *Pseudomonas*, examples of the vector can include generic host vector systems established in *Pseudomonas putida, Pseudomonas cepacia*, and the like; and the wide-host-range vector pKT240 (containing genes required for autonomous replication and derived from RSF1010 and the like), which is based on a plasmid involved in degradation of toluene compounds, TOL plasmid (Gene, 26, 273-82 (1983)).

For the genus *Brevibacterium*, especially *Brevibacterium lactofermentum*, examples of the vector can include plasmid vectors such as pAJ43 (Gene 39, 281 (1985)). As the promoter and the terminator, various promoters and terminators used for *E. coli* can be used.

For the genus *Corynebacterium*, especially *Corynebacterium glutamicum*, examples of the vector include plasmid vectors such as pCS11 (JP 57 (1982)-183799 A) and pCB101 (Mol. Gen. Genet. 196, 175 (1984)).

For *Saccharomyces*, especially *Saccharomyces cerevisiae*, examples of the vector include YRp-type, YEp-type, YCp-type, and YIp-type plasmids. Moreover, examples of promoters and terminators which may be used include those of the genes for various enzymes such as alcohol dehydrogenase, glyceraldehyde-3-phosphate dehydrogenase, acid phosphatase, β-galactosidase, phosphoglycerate kinase, and enolase.

For the genus *Schizosaccharomyces*, examples of the vector can include the plasmid vector derived from *Schizosaccharomyces pombe* described in Mol. Cell. Biol. 6, 80 (1986). In particular, pAUR224 is commercially available from Takara Bio Inc. and readily available.

In the genus *Aspergillus, Aspergillus niger, Aspergillus oryzae* and the like are the best-studied species among molds, in which plasmids and integration into the chromosome are applicable, and promoters for extracellularly secreted protease and amylase can be used (Trends in Biotechnology 7, 283-287 (1989)).

Moreover, host vector systems other than the above-described systems have also been established for various microorganisms and those systems may be used as appropriate.

Moreover, various host/vector systems have been established for plants and animals, in addition to microorganisms. In particular, systems for the expression of a large quantity of a heterogeneous protein in animals, such as insects (e.g., silkworm) (Nature 315,592-594 (1985)), or in plants, such as rapeseed, maize and potato, and systems utilizing cell-free protein synthesis systems based on a *E. coli* cell-free extract, wheat germ and the like have been established, which systems may be preferably used.

In the production method of the present invention, the 2-oxoglutarate-dependent L-pipecolic acid hydroxylase, the microorganism or cell having the ability to produce the enzyme, the processed product of the microorganism or cell, and/or the culture liquid comprising the enzyme and obtained by culturing the microorganism or cell may be allowed to act on the reaction substrate L-pipecolic acid in the presence of 2-oxoglutaric acid to produce cis-5-hydroxy-L-pipecolic acid.

The production method of the present invention is not particularly limited as long as it can allow 2-oxoglutaric acid and the 2-oxoglutarate-dependent L-pipecolic acid hydroxylase, the microorganism or cell having the ability to produce the enzyme, the processed product of the microorganism or cell, and/or the culture liquid comprising the enzyme and obtained by culturing the microorganism or cell, to act on L-pipecolic acid. However, it is usually preferable for the production method to be carried out in an aqueous medium or in a mixture of the aqueous medium and an organic solvent. It is further preferable for the production method of the present invention to be carried out in the presence of ferrous ion.

Examples of the aqueous medium include water and buffers.

Moreover, organic solvents in which the solubility of the reaction substrate is high may be used as the aforementioned organic solvent, including alcoholic solvents such as methanol, ethanol, 1-propanol, 2-propanol, 1-butanol, tert-butanol and the like, and acetone, and dimethyl sulfoxide. Moreover, other organic solvents effective in the removal of reaction by-products may also be used as the aforementioned organic solvent, including ethyl acetate, butyl acetate, toluene, chloroform, n-hexane and the like.

The reaction substrate L-pipecolic acid is usually used at a substrate concentration within the range of 0.01% w/v to 90% w/v, and preferably 0.1% w/v to 30% w/v. The reaction substrate may be added in one portion when the reaction is initiated, but is preferably added in a continuous or intermittent fashion in view of the inhibitory effect on the substrate of the enzyme, if any, to be reduced and the increase in the concentration of the accumulated product.

The number of moles of 2-oxoglutaric acid to be added is normally equivalent to or more than that of the substrate, and preferably in a range of 1 to 1.2 times as many as that of the substrate. The 2-oxoglutaric acid may be added in one portion when the reaction is initiated, but is desirably added in a continuous or intermittent fashion in view of the inhibitory effect on the substrate of the enzyme, if any, to be reduced and the increase in the concentration of the accumulated product. Alternatively, an inexpensive compound that can be metabolized by the host, such as glucose, may be added instead of 2-oxoglutaric acid, which compound is metabolized by the host and the resulting 2-oxoglutaric acid produced during this process may be used for the reaction.

The production method of the present invention is preferably carried out in the presence of ferrous ion. Preferably, the concentration of ferrous ion to be used is normally in a range of 0.01 mmol/L to 100 mmol/L, and preferably 0.1 mmol/L to 10 mmol/L. The ferrous ions may be added in one portion in the form of ferrous sulfate or the like when the reaction is initiated, while it is also effective to add further ferrous ions during the reaction in cases where the added ferrous ions have been oxidized to ferric ions or have decreased by precipitation formation. Moreover, in cases where a sufficient amount of ferrous ions are contained in the L-pipecolic acid hydroxylase, the microorganism or cell having the ability to produce the enzyme, the processed product of the microorganism or cell, and/or the culture liquid comprising the enzyme and obtained by culturing the microorganism or cell of the present invention, the addition of ferrous ion is not necessarily required.

The reaction is carried out at a reaction temperature of usually 4° C. to 60° C., preferably 15° C. to 45° C., and particularly preferably 20° C. to 40° C., and at a pH of usually 3 to 11, and preferably 5 to 8. The reaction time is usually from about 1 hour to about 72 hours.

The microorganism or cell, the processed product of the microorganism or cell, and/or the culture liquid comprising the enzyme and obtained by culturing the microorganism or cell is/are added to the reaction solution in such an amount that, for example, the concentration of the cell is normally in a range of about 0.1% w/v to about 50% w/v, and preferably 1% w/v to 20% w/v in terms of wet cell weight if the cell is added, and that the added amount of the processed product corresponds to the above-described cell concentration based on the calculated specific activity of the enzyme if the processed product is used.

Hydroxy-L-pipecolic acid produced by the production method of the present invention can be purified as follows: after the completion of the reaction, cells, proteins and the like in the reaction solution are separated by centrifugation, membrane filtration and the like; hydroxy-L-pipecolic acid is subsequently purified by an appropriate combination of extraction with an organic solvent, such as 1-butanol, tert-butanol and the like; distillation; column chromatography using an ion exchange resin and/or silica gel and the like; isoelectric precipitation; crystallization with a salt such as monohydrochloride salts, dihydrochloride salts and calcium salts; and the like.

EXAMPLES

Now, the present invention will be described in more detail by way of examples but is not limited thereto.

Example 1

Cloning of 2-oxoglutarate-dependent Pipecolic Acid Hydroxylase Genes

A gene sequence (xdph_Ecodon; SEQ ID NO: 1) encoding a putative L-proline cis-4-hydroxylase, XdPH (GenBank Accession No. CDG16639; SEQ ID NO: 4), from the *Xenorhabdus doucetiae* strain FRM16 and codon-optimized for expression in *E. coli* was artificially synthesized at DNA2.0, Inc. and then inserted into pJExpress411 (DNA2.0, Inc.) to produce the plasmid pJ411XdPH.

Genes for known representative enzymes exhibiting an activity to hydroxylase pipecolic acid at position 5 were also cloned in a similar way. The sruph_Ecodon (SEQ m NO: 3) and smph_Ecodon (SEQ ID NO: 2), which are gene sequences encoding the L-pipecolic acid cis-5-hydroxylase SruPH (GenBank Accession No. EFV12517; SEQ ID NO: 6) from the *Segniliparus rugosus* NBRC101839 strain and the L-proline cis-4-hydroxylase SmPH (GenBank Accession No. CAC47686; SEQ ID NO: 5) from the *Sinorhizobium meliloti* 1021 strain, respectively, and codon-optimized for expression in *E. coli*, were artificially synthesized at DNA2.0, Inc. and then inserted into pJexpress411 (DNA2.0, Inc) and pJexpress401, respectively, to produce the plasmids pJ411SruPH and pJ401SmPH. For the smph_Ecodon, the primers smph_f (SEQ ID NO: 7) and smph_r (SEQ ID NO: 8) were synthesized and used for PCR reaction using those primers and the plasmid DNA as a template according to a conventional method to obtain a DNA fragment with a length of about 1.0 kbp. The obtained DNA fragment was digested with the restriction enzymes Nde I and Hind III and then inserted according to a conventional method into pET24a (Novagen) digested with Nde I and Hind III to obtain pET24SmPH, respectively.

Example 2

Obtainment of 2-oxoglutarate-Dependent Pipecolic Acid Hydroxylase Gene-Expressing Bacteria and Confirmation of Expression Level Next, each of the obtained plasmids was used to transform *E. coli* (*Escherichia coli*) BL21 (DE3) (Invitrogen) according to a conventional method and thus to obtain recombinant *E. coli* BL21 (DE3) pJ411XdPH, BL21 (DE3)/pJ411SruPH, and BL21 (DE3)/pET24SmPH. To obtain bacteria expressing each of the introduced genes, each recombinant *E. coli* was cultured using liquid LB medium containing kanamycin and a lac promoter-inducible substance for 4 hours to 6 hours at 28° C. and then further cultured at 15° C. for about 40 hours, followed by harvest of bacteria.

Each of the obtained recombinant *E. coli* was suspended in 50 mmol/L MES (2-Morpholinoethanesulfonic acid) buffer at pH 7 to give a turbidity ($OD_{630}$) of about 10. The suspension with a volume of 0.5 mL was sonicated on ice and then centrifuged at a rotation rate of 12,000 rpm to separate supernatant and residue. The obtained supernatant was regarded as a soluble fraction, while the residue was regarded as an insoluble fraction.

The obtained soluble and insoluble fractions were processed according to a conventional method and the expression level of the expressed protein was subsequently confirmed by SDS-polyacrylamide electrophoresis. The result is shown in FIG. 1.

Example 3

Confirmation of 2-oxoglutarate-dependent Pipecolic Acid Hydroxylase Activity

A solution with a volume of 0.2 mL in a plastic tube, to which L-pipecolic acid, 2-oxoglutaric acid, L-ascorbic acid, and ferrous sulfate had been added to concentrations of 5 mmol/L, 10 mmol/L, 1 mmol/L, and 0.5 mmol/L, respectively, and each crude enzyme solution obtained in Example 2 had been added to a protein concentration of about 2 mg/mL, was shaken for one hour at 30° C.

Figure 2:
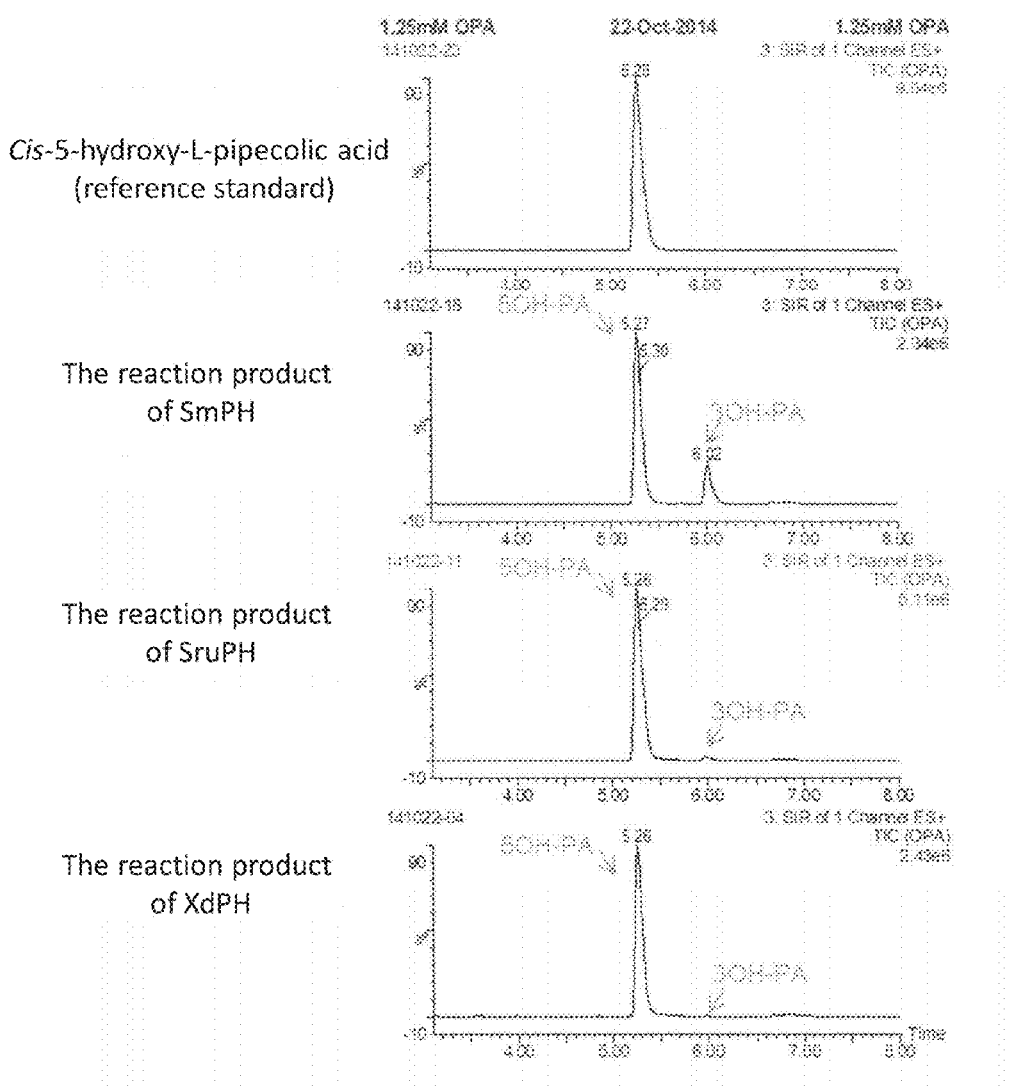
FIG. 2 shows the result of analysis on reaction products by the *E. coli* strains to which different L-pipecolic acid hydroxylase genes have been introduced.

The reaction products were derivatized with 1-fluoro-2,4-dinitrophenyl-5-L-alaninamide (FDAA) and then analyzed with UPMC-MS (Waters Corporation). Consequently, as shown in FIG. 2, the generation of a compound corresponding to the 5-hydroxy-pipecolic acid standard with a retention time of 5.3 minutes was confirmed in the solution after the reaction using each crude enzyme solution. The 5-hydroxy-pipecolic acid-generating activity (U/g) demonstrated by each of the enzyme solutions was calculated to be 4.1 U/g, 8.9 U/g, and 3.1 U/g of protein, respectively. A unit (U) herein represents the ability to generate 1 μmol of a substrate in the period of one minute.

Moreover, the generation of a compound with a retention time of 6.0 minutes, which is considered as cis-3-hydroxy-pipecolic acid, was confirmed in the reaction product of SmPH. The ratio of amount of cis-3-hydroxy-pipecolic acid to the amount of the total hydroxy pipecolic acids was compared based on the peak area values of hydroxy pipecolic acids on the chromatograms and the result of the comparison was presented in Table 2. It indicates that the generated cis-3-hydroxy-pipecolic acid in the reaction product of XdPH was as few as 0.17% of the total hydroxy pipecolic acids.

In addition, the analytical conditions for hydroxy pipecolic acids on HPLC are as shown in Table 1.

Example 4

Confirmation of Temperature Dependency of Hydroxylation Reaction

Figure 3:
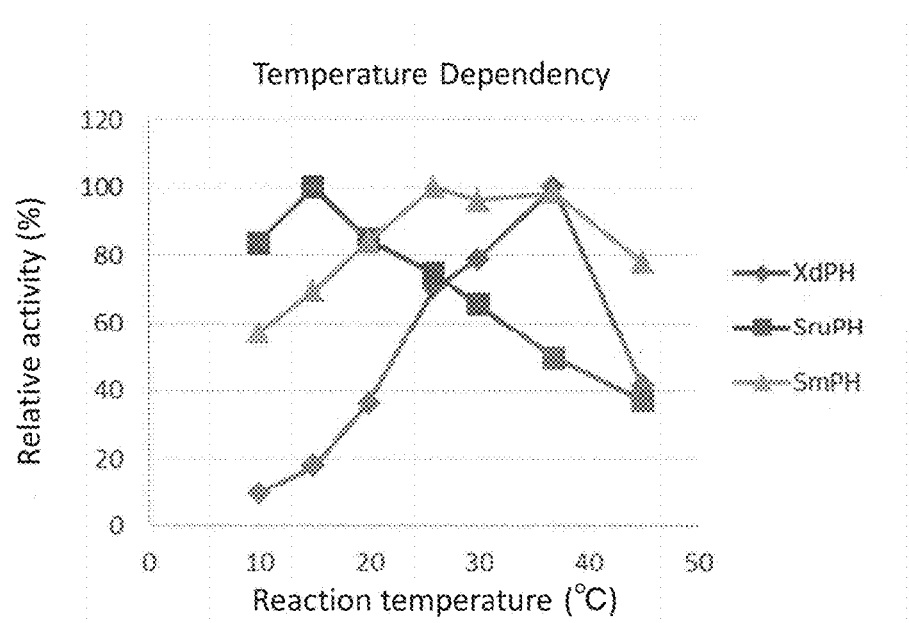
FIG. 3 shows the temperature dependency of the activity of different L-pipecolic acid hydroxylases.

To confirm the temperature dependency in each enzyme reaction, the crude enzyme solution of each hydroxylase was incubated at different temperatures for one hour and thirty minutes and then allowed to react at 30° C. for one hour to measure the amount of the thus-generated 5-hydroxy-pipecolic acid. The obtained results were presented in FIG. 3 as relative activity based on the highest activity value of each enzyme set as 100(%).

TABLE 1 a) LC settings

| | |
|---|---|
| Used equipment | ACQUITY SQD UPLC/MS (Waters Corporation) |
| Analytical column | ACQUITY UPLC BEH C18 Column, (Waters Corporation) |
| Column temperature | 30° C. |
| Eluent | A 0.1% formic acid/water solution |
| | B 0.1% formic acid/acetonitrile solution |

TABLE 1-continued b) Elution conditions

| Time (min) | A (%) | B (%) | Flow rate (mL/min) |
|---|---|---|---|
| 0 | 80 | 20 | 0.2 |
| 12 | 45 | 55 | |
| 12.5 | 0 | 100 | |
| 14.5 | 0 | 100 | |
| 14.6 | 80 | 20 | |
| 18 | 80 | 20 | | c) MS conditions

| | | |
|---|---|---|
| Used equipment | SQ Detector (Waters Corporation) | |
| Settings | Ion mode | ESI Positive |
| | Capillary Voltage (kV) | 3.0 |
| | Cone Voltage (V) | 50 |
| | Extractor Voltage (V) | 3 |
| | RF Lens Voltage (V) | 0.1 |
| | Source Temp. (° C.) | 130 |
| | Desolvation Temp. (° C.) | 350 |
| | Desolvation Gas Flow (L/hr) | 600 |
| | Cone Gas Flow (L/hr) | 50 |

TABLE 2

| | Peak area | | The ratio of amount of 3-hydroxy-pipecolic acid to the amount of the total hydroxy pipecolic acids (%) |
|---|---|---|---|
| Enzyme | 5OH-PA (area) | 3OH-PA (area) | |
| SmPH | 220516 | 49886 | 18.45 |
| SnuPH | 538144 | 9558 | 1.75 |
| XdPH | 220283 | 382 | 0.17 |

Example 5

Cloning of 2-Oxoglutarate-Dependent Pipecolic Acid Hydroxylase Genes

DNA fragments each having a length of about 1 kbp were amplified by polymerase chain reaction (PCR) using chromosome DNA from the *Xenorhabdus doucetiae* strain FRM16, and the strain PR06-A of its relative species, *Xenorhabdus romanii*, as templates and the primers XdPH-fus-f (SEQ ID NO: 12) and XdPHfus-r (SEQ ID NO: 13), which are primers that allow the gene for a putative L-proline cis-4-hydroxylase, XdPH (XdPHori: GenBank Accession No. FO704550-XDD1_0936), to be amplified. The obtained two DNA fragments were inserted using In-fusion HD Cloning Kit (Takara Bio Inc.) according to a conventional method into pQE60 (QIAGEN N.V.) digested with the restriction enzymes Nco I and Hind III to obtain pQEXdPHori and pQEXrPHori, respectively.

Next, each of the obtained plasmids was used to transform *E. coli* (*Escherichia coli*) JM109 according to a conventional method and thus to obtain recombinant *E. coli* JM109/pQEXdPHori and JM109/pQEXrPHori. The gene sequence of the amino acid hydroxylase from the *Xenorhabdus romanii* strain PR06-A (xrph_ori; SEQ ID NO: 10) and the amino acid sequence thereof (XrPH; SEQ ID NO: 11) were determined by identifying the gene sequence inserted into pQE60 according to a conventional method. XrPH had an identity of 99% to XdPH.

To obtain bacteria expressing each of the introduced genes, each recombinant *E. coli* was cultured overnight using liquid LB medium containing ampicillin, followed by harvest of bacteria.

In a plastic tube, 20 mmol/L L-pipecolic acid, 15 mmol/L 2-oxoglutaric acid, 10 mmol/L Tris(2-carboxyethyl)phosphine hydrochloride (TCEP), 0.5 mmol/L ferrous sulfate, 10 mmol/L sodium citrate, 1% Nymeen, and 0.2 mL of a suspension of bacteria in 50 mmol/L Bis(2-hydroxyethyl)iminotris(hydroxymethyl)methane buffer at pH 6.5, which had been obtained from 0.4 mL of the culture liquid of either of the obtained recombinant *E. coli* JM109/pQEXdPHori and JM109/pQEXrPHori, were placed to produce a reaction solution with a total volume of 1 mL and then this reaction solution was shaken for 20 hours at 20° C.

The solution after the reaction was derivatized by using AccQ-Tag (Waters Corporation) and then analyzed under the conditions below for HPLC to measure the generated 5-hydroxy-L-pipecolic acid:

Column: XBridge C18 5 µm (2.1×150 mm) (Waters Corporation);
Eluent A: 10 mmol/L ammonium acetate (pH 5);
Eluent B: methanol (0 to 0.5 min (from 0% to 1%), 0.5 to 18 min (from 1% to 5%), 18 to 19 ruin (from 5% to 9%), 19 to 29.5 min (from 9% to 17%), 29.5 to 40 min (from 17% to 60%), 40 to 43 min (60%));
Flow rate: 0.3 mL/min;
Detection: fluorescence detector;
Temperature: 30° C.

The result of the measurement is shown in Table 3. It was confirmed that, the activity to hydroxylate pipecolic acid at position 5 was retained not only in the hydroxylase XdPH from the *Xenorhabdus doucetiae* strain FRM16 but also in the hydroxylase from the *Xenorhabdus romanii* strain PR06-A.

TABLE 3

| Enzyme | Retention time (min) | Peak area of 5-hydroxy-L-pipecolic acid | Relative activity (%) |
|---|---|---|---|
| XdPH | 20.7 | 637895 | 100 |
| XrPH | 20.7 | 192647 | 30 |

The invention claimed is:

1. A method for producing cis-5-hydroxy-L-pipecolic acid, the method comprising allowing a 2-oxoglutarate-dependent L-pipecolic acid hydroxylase, a microorganism or cell that produces the enzyme, a processed product of the microorganism or cell having the enzyme, and/or a culture liquid comprising the enzyme and obtained by culturing the microorganism or cell, to act on L-pipecolic acid to generate cis-5-hydroxy-L-pipecolic acid,
wherein the 2-oxoglutarate-dependent L-pipecolic acid hydroxylase comprises:
(A) a polypeptide comprising the amino acid sequence of SEQ ID NO: 4 or 11;
(B) a polypeptide comprising the amino acid sequence of SEQ ID NO: 4 or 11 except that 1 to 10 amino acids are deleted, substituted, and/or added, wherein said polypeptide has 2-oxoglutarate-dependent L-pipecolic acid hydroxylase activity; or
(C) a polypeptide comprising an amino acid sequence with an identity of not less than 90% to the amino acid sequence of SEQ ID NO: 4 or 11, wherein said polypeptide has 2-oxoglutarate-dependent L-pipecolic acid hydroxylase activity.

2. The method for producing cis-5-hydroxy-L-pipecolic acid according to claim 1, wherein DNA encoding the 2-oxoglutarate-dependent L-pipecolic acid hydroxylase comprises:
(a) DNA comprising the nucleotide sequence of SEQ ID NO: 1 or 10;
(b) DNA comprising the nucleotide sequence of SEQ ID NO: 1 or 10 except that 1 to 30 nucleotides are substituted, deleted, and/or added, wherein said DNA encodes a polypeptide having 2-oxoglutarate-dependent L-pipecolic acid hydroxylase activity; or
(c) DNA which hybridizes with the full-length complementary strand of the polynucleotide of SEQ ID NO: 1 or 10 under stringent conditions, wherein the conditions comprise a hybridization at 65° C. in the presence of 0.7 mol/L to 1.0 mol/L sodium chloride aqueous solution and a washing under a temperature condition of 65° C. by using one solution with an SSC concentration ranging from 0.1 to 2×SSC (the composition of 1×SSC: 150 mmol/L sodium chloride aqueous solution, 15 mmol/L sodium citrate aqueous solution), wherein said DNA encodes a polypeptide having 2-oxoglutarate-dependent L-pipecolic acid hydroxylase activity.

3. The method for producing cis-5-hydroxy-L-pipecolic acid according to claim 1, wherein the 2-oxoglutarate-dependent L-pipecolic acid hydroxylase, the microorganism or cell that produces the enzyme, the processed product of the microorganism or cell having the enzyme, and/or the culture liquid comprising the enzyme and obtained by culturing the microorganism or cell is/are allowed to act on said L-pipecolic acid in the presence of 2-oxoglutaric acid and a ferrous ion.

4. The method for producing cis-5-hydroxy-L-pipecolic acid according to claim 2, wherein the 2-oxoglutarate-dependent L-pipecolic acid hydroxylase, the microorganism or cell that produces the enzyme, the processed product of the microorganism or cell having the enzyme, and/or the culture liquid comprising the enzyme and obtained by culturing the microorganism or cell is/are allowed to act on said L-pipecolic acid in the presence of 2-oxoglutaric acid and a ferrous ion.

5. A 2-oxoglutarate-dependent L-pipecolic acid hydroxylase protein having an activity to act on L-pipecolic acid to generate cis-5-hydroxy-L-pipecolic acid, wherein said 2-oxoglutarate-dependent L-pipecolic acid hydroxylase protein comprises:
a polypeptide comprising the amino acid sequence of SEQ ID NO: 4 or 11 except that 1-10 amino acids are substituted and/or added, wherein said polypeptide has 2-oxoglutarate-dependent L-pipecolic acid hydroxylase activity.

* * * * *